US012150669B2

(12) United States Patent
Menn (10) Patent No.: US 12,150,669 B2
(45) Date of Patent: Nov. 26, 2024

(54) SYSTEM FOR AXIAL POSITIONING OF A ROTATING SHAFT

(71) Applicant: MOST Cardio, LLC, Salem, MA (US)

(72) Inventor: Pavel Menn, Salem, MA (US)

( * ) Notice: Subject to any disclaimer, the term of this patent is extended or adjusted under 35 U.S.C. 154(b) by 0 days.

(21) Appl. No.: 18/390,860

(22) Filed: Dec. 20, 2023

(65) Prior Publication Data

US 2024/0206905 A1 Jun. 27, 2024

Related U.S. Application Data

(60) Provisional application No. 63/477,253, filed on Dec. 27, 2022.

(51) Int. Cl.
*A61B 17/3207* (2006.01)
*A61B 17/00* (2006.01)
*B65H 51/10* (2006.01)

(52) U.S. Cl.
CPC .......... *A61B 17/320758* (2013.01); *A61B 2017/00292* (2013.01); *A61B 2017/00398* (2013.01); *A61B 2017/00982* (2013.01); *A61B 2560/0443* (2013.01); *B65H 51/10* (2013.01)

(58) Field of Classification Search
CPC ...... A61B 17/320725; A61B 17/32075; A61B 17/320783; A61B 17/320758; A61B 34/30; A61B 2034/301; A61B 2034/304
See application file for complete search history.

(56) References Cited

U.S. PATENT DOCUMENTS

| 8,870,815 | B2 * | 10/2014 | Bhat | A61B 8/42 604/95.01 |
|---|---|---|---|---|
| 2005/0028628 | A1 * | 2/2005 | Liue | H02K 49/102 74/DIG. 4 |
| 2017/0176946 | A1 * | 6/2017 | Junod | G04C 3/101 |
| 2018/0168753 | A1 * | 6/2018 | Scheib | A61B 90/06 |

* cited by examiner

*Primary Examiner* — Tuan V Nguyen
(74) *Attorney, Agent, or Firm* — Saul Ewing LLP; Brian R. Landry (57) ABSTRACT

A system for axial positioning of a rotating shaft is provided herein. The system includes a first wheel. The system also includes a second wheel positioned adjacent to the first wheel such that the first wheel and second wheel are configured to rotate in opposite directions. The second wheel is also positioned such that first wheel and second wheel are configured to exert axial force tangential to the first wheel and the second wheel to a shaft positioned between the first wheel and the second wheel. Each of the first wheel and the second wheel each comprise a plurality of rollers positioned tangentially along a circumference of the first wheel and the second wheel.

14 Claims, 7 Drawing Sheets

SYSTEM FOR AXIAL POSITIONING OF A ROTATING SHAFT

CROSS-REFERENCE TO RELATED APPLICATION(S)

This application claims the benefit of priority under 35 U.S.C. § 119(e) to U.S. Provisional Patent Application Ser. No. 63/477,253, filed Dec. 27, 2022. The entire contents of each application is hereby incorporated by reference herein.

BACKGROUND

Atherosclerosis is a form of arteriosclerosis in which plaque accumulates in an arterial vessel and the artery wall thickens as a result of invasion and accumulation of white blood cells on the inner artery vessel walls. These plaque accumulations contain both living, active WBCs (producing inflammation) and remnants of dead cells, including cholesterol and triglycerides. The remnants eventually include calcium and other crystallized materials, to form plaque. The plaque reduces the elasticity of the artery vessel walls. It is commonly referred to as a "hardening" or furring of the arteries.

Over time these plaques can become large enough to reduce or occlude blood flow through the vessels, leading to symptoms of low blood flow. To treat this disease blood flow must be restored through the vessel, by removing or reducing the size of these plaques.

SUMMARY OF THE INVENTION

One aspect of the invention provides a system for axial positioning of a rotating shaft. The system includes: a first wheel; and a second wheel positioned adjacent to the first wheel such that the first wheel and second wheel: are configured to rotate in opposite directions; and are configured to exert axial force tangential to the first wheel and the second wheel to a shaft positioned between the first wheel and the second wheel. Each of the first wheel and the second wheel each include a plurality of rollers positioned tangentially along a circumference of the first wheel and the second wheel.

This aspect of the invention can have a variety of embodiments. The first wheel can include two axially offset rings of rollers. The second wheel can include a single ring of rollers.

The first wheel and the second wheel can be each configured to be driven by a ferromagnetic coupling. At least one of the first wheel and the second wheel can be configured to be driven by a ferromagnetic coupling. The first wheel can include a plurality of magnets configured to be magnetically coupled to a second magnet and driven by a drive system.

The system can further include: a rod coupled to the second wheel, the rod being configured to translate second wheel to allow loading of a shaft; and a spring, the spring being connected to the rod such that the spring can impose a spring force on the rod. The system can further include a lever pivotally coupled to the rod.

The first wheel can include a first subwheel and a second subwheel. The system can further include a housing portion at least partially enclosing the first wheel and the second wheel.

Another aspect of the invention provides a system for axial positioning of a rotating shaft. The system includes: a shaft; a first wheel; and a second wheel positioned adjacent to the first wheel such that the first wheel and second wheel: are configured to rotate in opposite directions; and are configured to exert axial force tangential to the first wheel and the second wheel to the shaft, the shaft being positioned between the first wheel and the second wheel. Each of the first wheel and the second wheel include a plurality of rollers positioned tangentially along a respective circumference of the first wheel and the second wheel.

This aspect of the invention can have a variety of embodiments. The shaft can be selected from the group consisting of: a rotating shaft, a catheter, and a rotating catheter.

Another aspect of the invention provides a method of axial positioning of a rotating shaft. The method includes: (a) providing a first wheel and a second wheel, wherein each of the first wheel and the second wheel comprise a plurality of rollers positioned tangentially along a respective circumference of the first wheel and the second wheel; (b) positioning a second wheel adjacent to the first wheel such that the first wheel and second wheel: are configured to rotate in opposite directions; and are configured to exert axial force tangential to the first wheel and the second wheel to the shaft, the shaft being positioned between the first wheel and the second wheel; (c) providing a rotating shaft disposed between the first wheel and the second wheel; and (d) rotating the first wheel such that the first wheel exerts an axial force tangential to the first wheel on the rotating shaft.

Another aspect of the invention provides a system for translating motion across a sterility drape. The system includes: a driving member, the driving member including: a first housing; and a first wheel within the first housing, the first wheel including a first magnet; and a driven member, the driven member including: a second housing; and a second wheel within the second housing, the second wheel including a second magnet. The driven member can be removably mounted on the driving member over a sterility drape applied to the driving member such that rotational force can be transferred through magnetic coupling across the first housing, the sterility drape, and the second housing.

This aspect of the invention can have a variety of embodiments. The first magnet of the driving member can be a first plurality of magnets and the second magnet of the driven member can be a second plurality of magnets. The second plurality of magnets can have a corresponding number of magnets to the first plurality of magnets.

DEFINITIONS

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

DETAILED DESCRIPTION OF THE INVENTION

Various types of atherectomy catheters and devices have been used to remove unwanted plaque from blood vessels to open the vessel and improve blood flow. Atherectomy catheters and devices are intravascular devices that mechanically remove plaque from the artery vessel walls.

However, atherectomy catheters and devices often undesirably cut, perforate, tear and stretch the vessel, causing scar formation. Such scar tissue causes inflammation, stenosis and blocks flow in the vessel and often needs to be removed. Furthermore, atherectomy catheters often run at high speeds causing heating damage to the vessels.

Atherectomy catheters block arterial blood flow completely during plaque removal, resulting in high vessel blood pressure, and posing a danger to the patient. Certain rotating shafts (e.g., catheters) may be difficult to control and/or provide during a procedure to remove plaque from a vessel.

The present disclosure describes a system useful in connection with the removal occlusive material from a vessel. In certain applications, a rotating shaft (e.g., shaft 112 of FIG. 2; various shafts, rotating shafts, catheters, catheter atherectors, and devices described in U.S. Pat. No. 10,687, 844, etc.) may be inserted into a vessel (e.g., a blood vessel) to aid in the removal of occlusive material, which may cause blockages (e.g., blocking or restricting blood flow) in blood vessels or similar harmful effects in a body. In order to provide, move, and/or guide such a rotating shaft, a system of the present disclosure may be used.

Figures 1A, 1B:
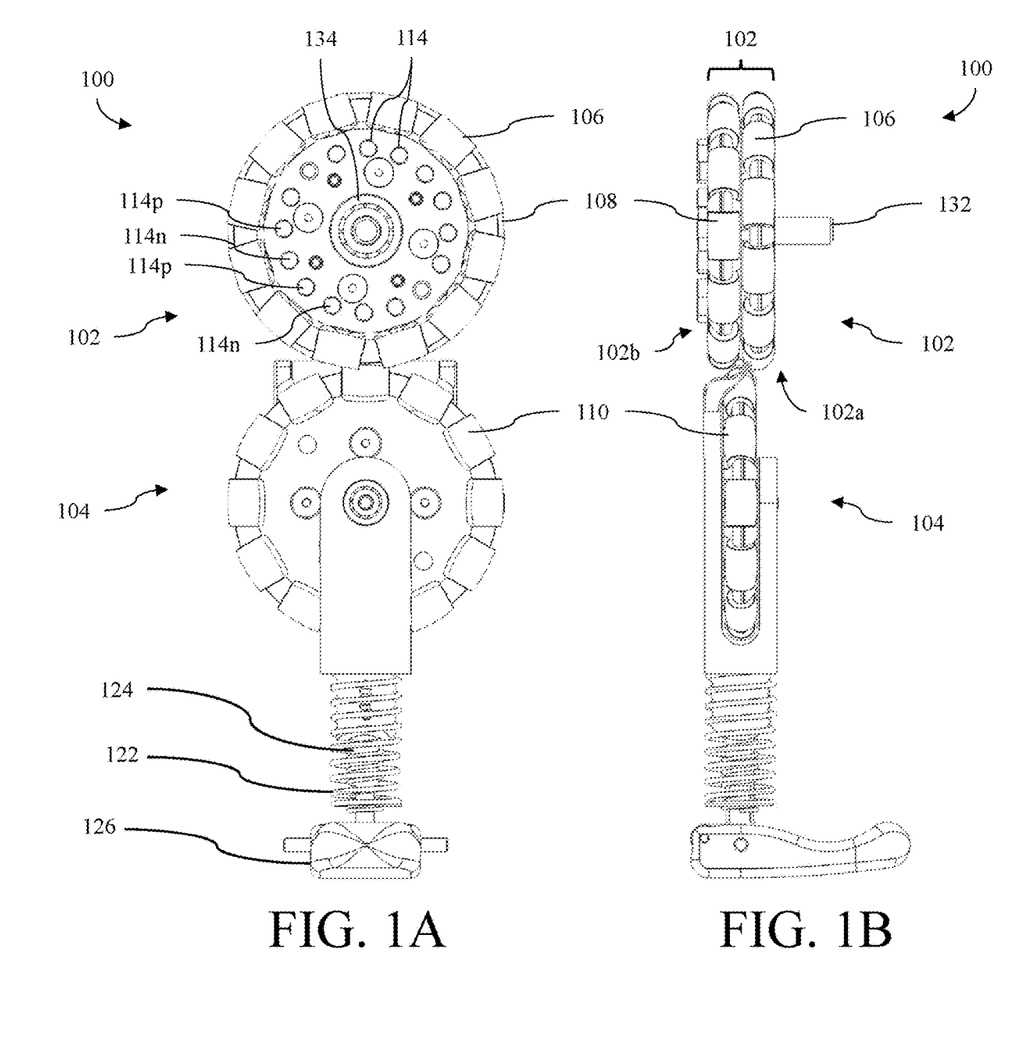
FIGS. 1A-1B illustrate a system for axial positioning of a rotating shaft, in accordance with an exemplary embodiment of the present disclosure.

The present disclosure is best described in connection with the drawings. Referring now to FIGS. 1A-1B, a system 100 for axial positioning of a rotating shaft is illustrated. System 100 includes a first wheel 102 and a second wheel 104, where second wheel 104 is positioned adjacent to first wheel 102. First wheel 102 and second wheel 104 are positioned such that first wheel 102 and second wheel 104 are configured to rotate in opposite directions (e.g., first wheel 102 rotates clockwise while and second wheel 104 rotates counterclockwise, or vice versa). The opposite rotation can be the result of first wheel 102 driving second wheel 104.

First wheel 102 can include a plurality of rollers 106 and rollers 108 positioned tangentially along a circumference of first wheel 102. First wheel 102 can include two axially offset rings of rollers (i.e., where the first ring includes rollers 106 and the second ring includes rollers 108). First wheel 102 is illustrated including two subwheels 102a and 102b, where the plurality of rollers 106 are positioned tangentially along a circumference of subwheel 102a and the plurality of rollers 108 are positioned tangentially along a circumference of subwheel 102b. Rollers 106 on subwheels 102a, 102b can be radially offset when assembled to promote continuous contact with shaft 112.

Similarly, second wheel 104 can include a plurality of rollers 110 positioned tangentially along a circumference of second wheel 104. Second wheel 104 can include a single ring of rollers 110. In certain embodiments, subwheels 102a and 102b do not touch each other.

A contact portion of the plurality of rollers 106, 108, 110 can be made of or include a low-friction material (e.g., a plastic material, a polymer, polytetrafluoroethylene (PTFE), a plastic material with a PTFE coating, etc.) such that friction of shaft 112 (e.g., rotating shaft) can be minimized. Another portion (e.g., a non-contact portion, an inner portion, etc.) of the plurality of rollers 106, 108, 110 can be made of or include a metallic material (e.g., steel, stainless steel, etc.).

In certain applications, a shaft (e.g., a rotating shaft, shaft 112 of FIG. 2, etc.) can be used between first wheel 102 and second wheel 104. Each of first wheel 102 and second wheel 104 are configured to exert axial forces tangential to first wheel 102 and second wheel 104 to a shaft positioned between first wheel 102 and second wheel 104. The plurality of rollers 108, 106, and/or 110 can rotate (e.g., passively) around the respective axis of each roller such that a rotational motion of a rotating shaft (e.g., the rotational motion being around the longitudinal axis of the shaft) is not impeded or impaired.

In certain embodiments, system 100 can include a spring 122, a rod 124 (e.g., a spring-loaded rod), and/or a lever 126. Spring 122 can be connected to rod 124 such that the spring can impose a spring force on rod 124. In certain embodiments, lever 126 can be pivotally coupled to rod 124 and rod 124 can be coupled (e.g., indirectly) to wheel 104. In such an embodiment, rod 124 can be configured to translate wheel 104 (e.g., pulling wheel 104 along the Y direction by depressing or actuating lever 126) to allow loading of a shaft (e.g., a rotating shaft, shaft 112 of FIG. 2, etc.).

In certain embodiments, system 100 can include an element 114 (e.g., a magnet, a bar magnet, a neodymium magnet, a metallic plate, a magnetizable steel plate, etc.) configured to be driven by a ferromagnetic coupling. In certain embodiments, such an element can be attached to first wheel 102 (e.g., attached to an outer surface). In certain embodiments, such an element can be embedded within first wheel 102 (e.g., between subwheels 102a and 102b, within subwheel 102a, within subwheel 102b, etc.). In certain embodiments, such an element can be a magnet at the bottom of first wheel 102 covered by a housing. In certain embodiments, such an element can be attached to or embedded within second wheel 104.

In one application, a plurality of elements 114 (e.g., magnets, neodymium magnets, etc.) can be used in connection with an electromagnetic drive system (e.g., including a servo drive, a servo controller, etc.) to control the position (i.e., translation) of at least a portion of a shaft (e.g., a rotating shaft). For example, in one embodiment, first wheel 102 can include a first plurality of magnets (e.g., element 114) configured to be magnetically coupled to a second magnet (or plurality of magnets) distinct from the plurality of magnets, wherein the first wheel, the plurality of magnets, and the second magnet can be driven by a driving element (e.g., a drive system, an electromagnetic drive system, etc.). In such an embodiment (and similar embodiments), the strength of the magnetic force between the first plurality of magnets of the first wheel and the second plurality of magnets can be adjusted or configured such that the first wheel is configured to not be over-torqued. In other words, the first wheel can be configured to decouple or exhibit "slippage" once a certain resistive torque is generated. For example, when the first and second plurality of magnets are configured to decouple at torque values greater than 1.5 in-oz, the driving torque of the driving element will not exceed applying 1.5 in-oz of torque to the first wheel. Such a feature can be useful as a safety feature (e.g., to not damage a rotating shaft, to not translate a rotating shaft too quickly, etc.). For example, such a feature may prevent damage to a patient or the device if a user of the driving element attempts to accelerate or translate a shaft too quickly or when a shaft is stuck or misaligned, thereby generating a resistive torque or force in the shaft and the first wheel.

In certain embodiments, system 100 can include a plurality of elements 114, wherein the plurality of elements 114 are magnets with alternating polarity. For example, referring specifically to FIG. 1A, element 114p can be a magnet with the positive (+) pole pointing out of the page. Further, element 114n can be a magnet with the negative (−) pole pointing out of the page. As illustrated, elements 114p and elements 114n can be distributed circumferentially with alternating polarities.

In certain embodiments, system 100 can include a magnetizable plate that can be placed (e.g., near at least one of element 114, near wheel 102, etc.) to contain magnetic flux. In certain embodiments, this can be positioned within, on, or near a driving mechanism.

In certain embodiments, system 100 can include a pin 132 (e.g., a dowel pin) and a bearing 134 (e.g., ball bearing) which wheel 102 can rotate about. In other embodiments, wheel 102 may be driven by pin 132 (e.g., where pin 132 mechanically coupled to wheel 102 without a bearing; where pin 132 is a pinion driven by connecting gear, rack, or similar driving mechanism; etc.).

In certain embodiments, the diameter of the single wheel (e.g., second wheel 104) is larger than the diameter of each of subwheels 102a and 102b.

Figure 2:
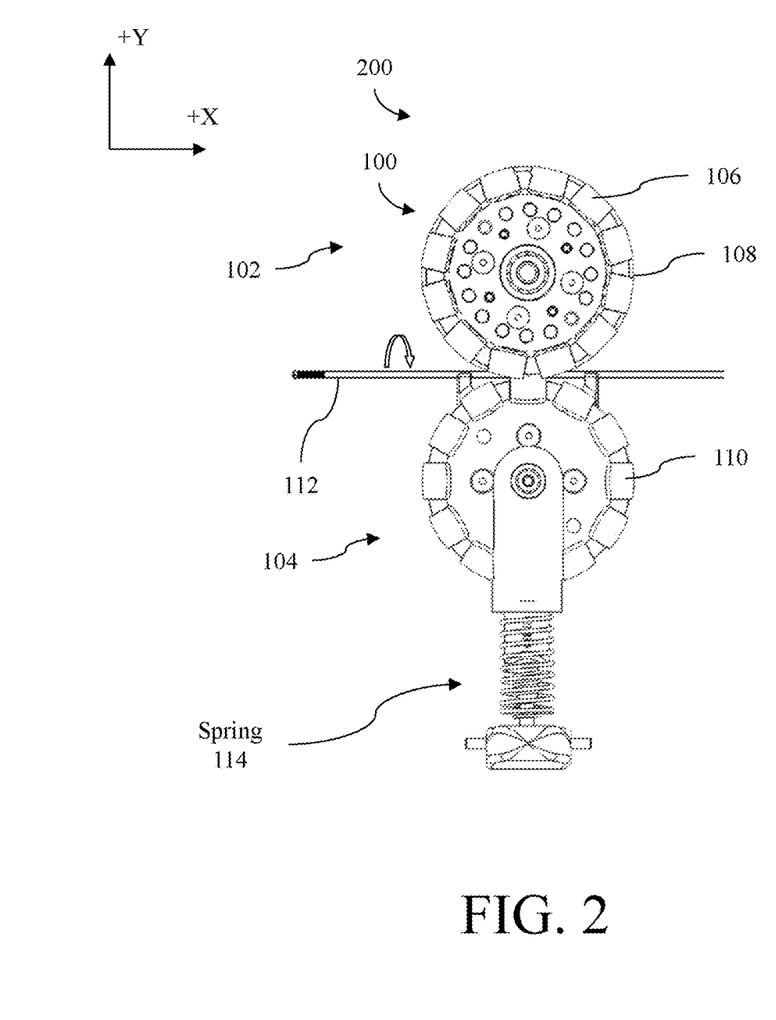
FIGS. 2-3 illustrate systems for axial positioning of a rotating shaft in connection with a portion of the shaft, in accordance with exemplary embodiments of the present disclosure.

Referring now to FIG. 2, a system 200 for axial positioning of a rotating shaft is illustrated. System 200 includes system 100, with like elements described in connection with FIG. 1. System 200 also includes a shaft 112 (e.g., a rotating shaft, a catheter, a rotating catheter, etc.). In certain embodiments, shaft 112 may be described as a "rotating" shaft, where at least a portion of the shaft rotates along a longitudinal axis of the shaft (or at least a portion of the shaft). In certain embodiments, the shaft can include materials, such as a flexible or pliable material; braided wire materials; polymers; fiber reinforced polymers; low-friction plastics; fiber reinforced PTFE; stainless steel; and/or other materials suitable for biomedical applications.

As shaft 112 is moved along the X-axis, shaft 112 rotates about the X-axis (as illustrated by an arrow in FIG. 2). Consequently, the plurality of rollers 106, 108, and 110 can rotate (e.g., passively) as desired for a given application. For example, when shaft 112 is rotating in connection with a plaque removal application, the rollers 106, 108, and 110 can allow such rotation even while spring 122 applies a compressive force (e.g., indirectly) on shaft 112 through wheel 104.

In certain embodiments, the shaft can be a catheter. One example of such an embodiment may be described as: a catheter with a hollow elongated lumen, a proximal opening, and a distal opening, an emulsification reduction of plaque particles sphere within the distal opening of the catheter, wherein the emulsification reduction of plaque particles sphere includes a substantially spherical shape composed of a plurality of alternating, adjacent protrusions and slots, wherein each protrusion includes a substantially smooth, curved surface extending outward, and a distal sharp tip, and each slot includes a substantially smooth, curved sharp bottom surface extending inward; an opening on the emulsification reduction of plaque particles sphere into the distal opening of the catheter within the plurality of protrusions and slots; an emulsification-extraction wire contained within the lumen of catheter, wherein the emulsification-extraction wire includes a substantially cylindrical screw helical ridge body and forms an internal auger within internal walls of the catheter lumen; a plurality of occlusive material cutters on the distal end of the emulsification-extraction wire extending outwardly from the distal opening of the catheter, wherein the plurality of occlusive material cutters are contained within the plurality of protrusions on the emulsification of plaque particles sphere; wherein the emulsification reduction of plaque particles sphere and the emulsification-extraction wire are configured to each independently rotate in opposite directions and move axially inside the vessel to engage the occlusive material; wherein the plurality of protrusions shave and scoop the occlusive material into the plurality of occlusive material cutters for emulsification into reduced particles, and the plurality of protrusions are configured such that the movement of the plurality of protrusions does not pierce or cut the vessel wall; wherein the distal sharp tips of each protrusion shave the occlusive material into the plurality of occlusive material particles for emulsification and distal sharp tips are configured to not contact the vessel wall; and wherein the mixture of emulsified occlusive material and blood only flows in a proximal direction into the catheter lumen through the plurality of occlusive material helical walls of the extraction wire cutters, wherein the mixture of emulsified occlusive material and blood is filtered and flows back into the vessel.

Figure 3:
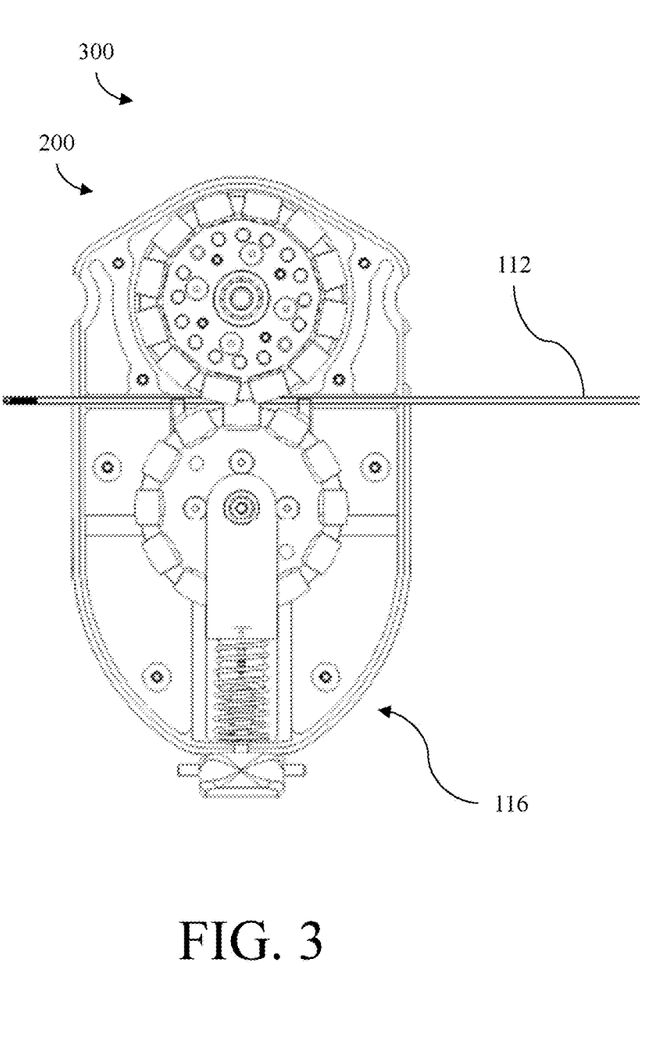

Referring now to FIG. 3, a system 300 for axial positioning of a rotating shaft is illustrated. System 300 includes system 200, with like elements described in connection with FIG. 1 and/or FIG. 2. System 300 also includes a housing portion 116 (e.g., a first housing portion, a rear housing portion, etc.) at least partially enclosing first wheel 102 and second wheel 104.

Figure 4:
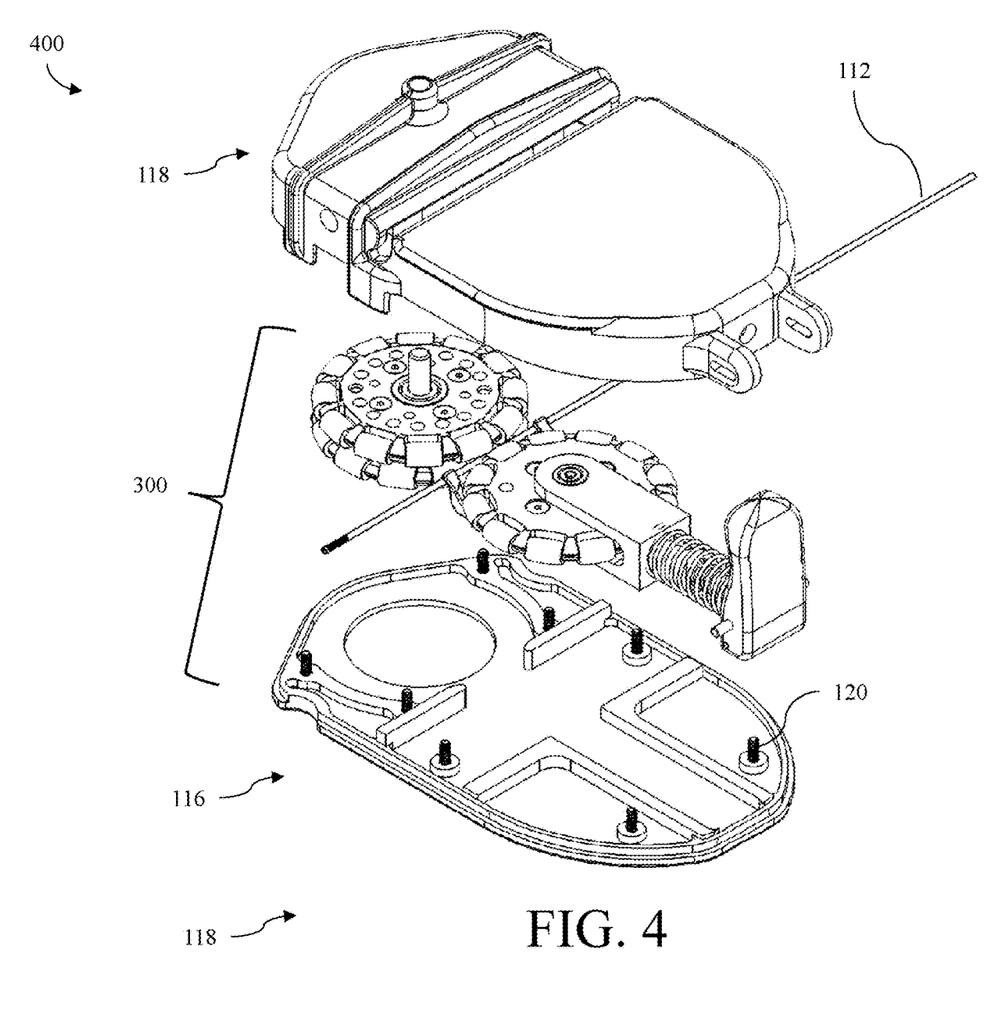
FIG. 4 illustrates an exploded perspective view of a system for axial positioning of a rotating shaft, in accordance with an exemplary embodiment of the present disclosure.

Referring now to FIG. 4, a system 400 for axial positioning of a rotating shaft is illustrated. System 400 includes system 300, with like elements described in connection with FIG. 1, FIG. 2, and/or FIG. 3. System 400 also includes a housing portion 118 (e.g., a second housing portion, a frontal housing portion, etc.) at least partially enclosing first wheel 102 and second wheel 104. Housing portion 116 and housing portion 118 (which can collectively be referred to as a "housing") can be mechanically connected using at least one fastening element 120 (e.g., a screw, a bolt, a rivet, a threaded rod, a coupling element, etc.). In certain embodiments, system 400 (including housing portion 116 and housing portion 118) can be configured to be disposable.

Figure 5A:
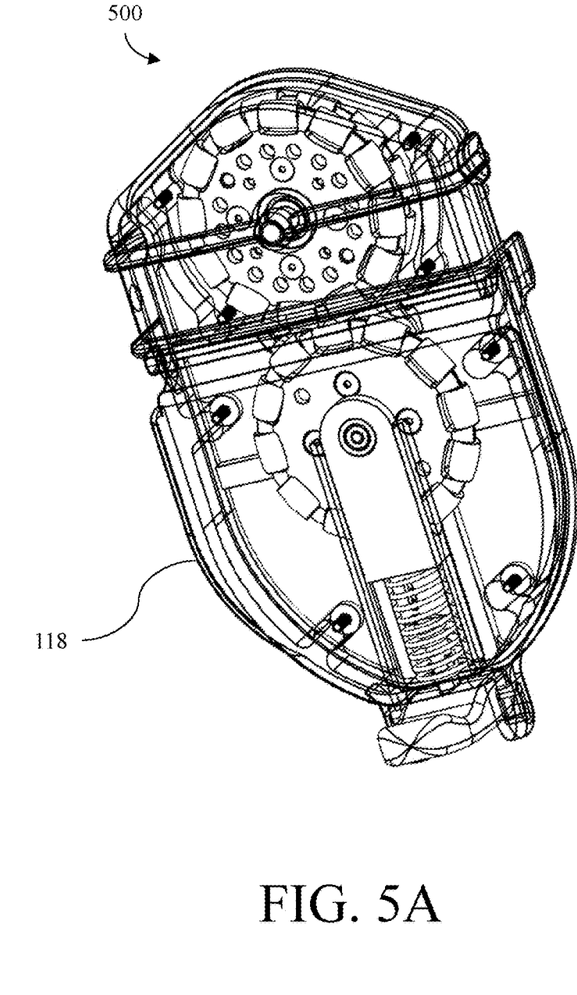
FIGS. 5A-5D illustrate various perspective and cross-sectional views of a system for axial positioning of a rotating shaft, in accordance with an exemplary embodiment of the present disclosure.
Figure 5B:
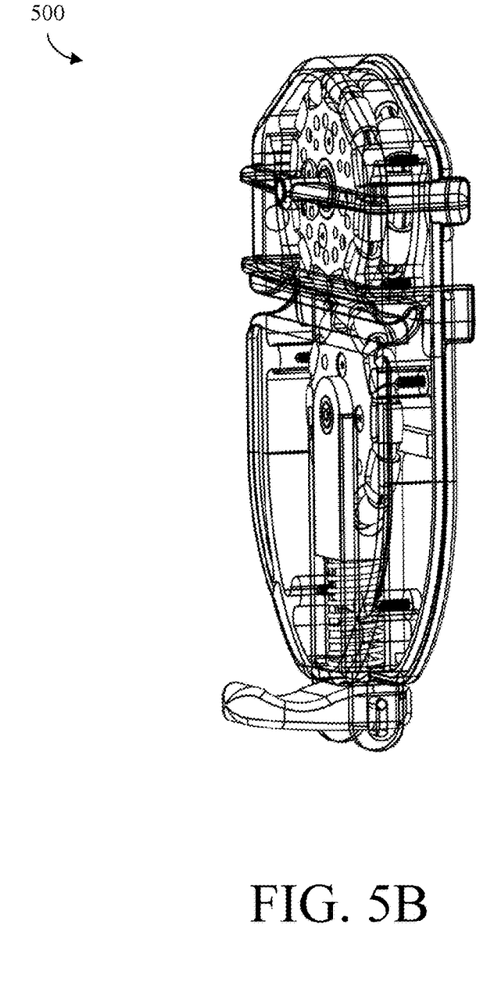
Figure 5C:
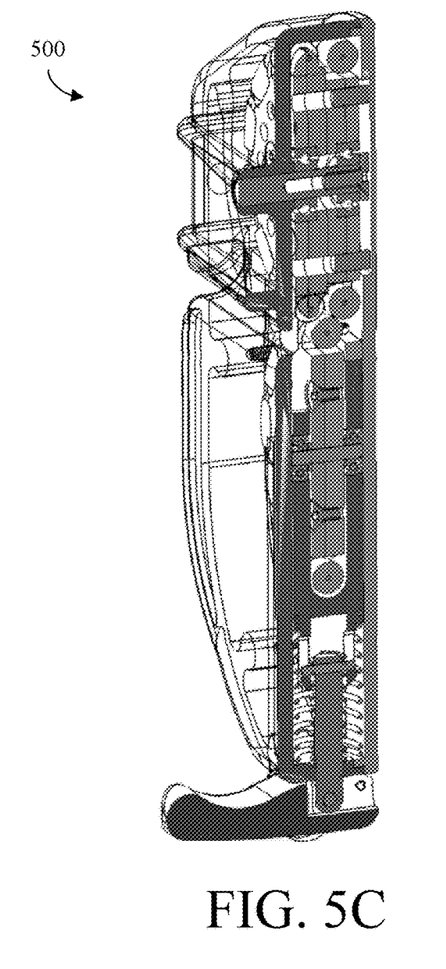
Figure 5D:
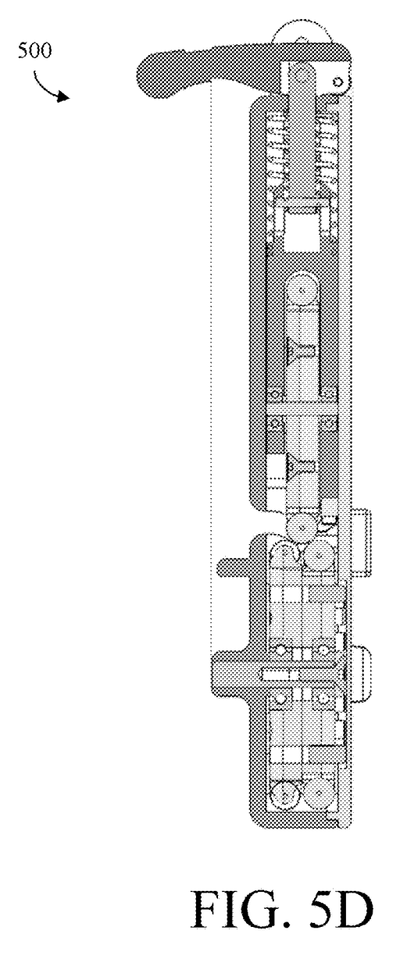

Referring now to FIGS. 5A-5D, a system 500 for axial positioning of a rotating shaft is illustrated. System 500 is substantially the same system as system 400 described in connection with FIG. 4, except shaft 112 is not illustrated. Referring specifically to FIG. 5A, a perspective view of system 500 is illustrated, with various elements (e.g., housing portion 118) illustrated in a transparent configuration for clarity. Referring specifically to FIG. 5B, a perspective view of system 500 is illustrated. Referring specifically to FIG. 5C, a perspective cross-sectional view of system 500 is illustrated. Referring specifically to FIG. 5D, a cross-sectional side view of system 500 is illustrated.

Figure 6:
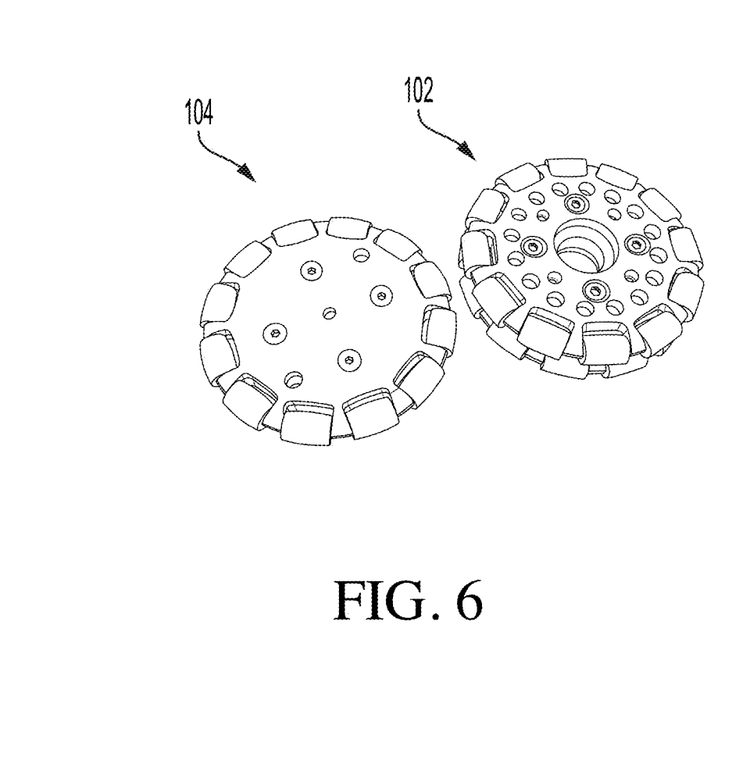
FIG. 6 illustrates a perspective view of wheels in accordance with an exemplary embodiment of the present disclosure.

Referring now to FIG. 6, perspective view of one embodiment (e.g., a prototype) of first wheel 102 and second wheel 104 is illustrated.

Figure 7:
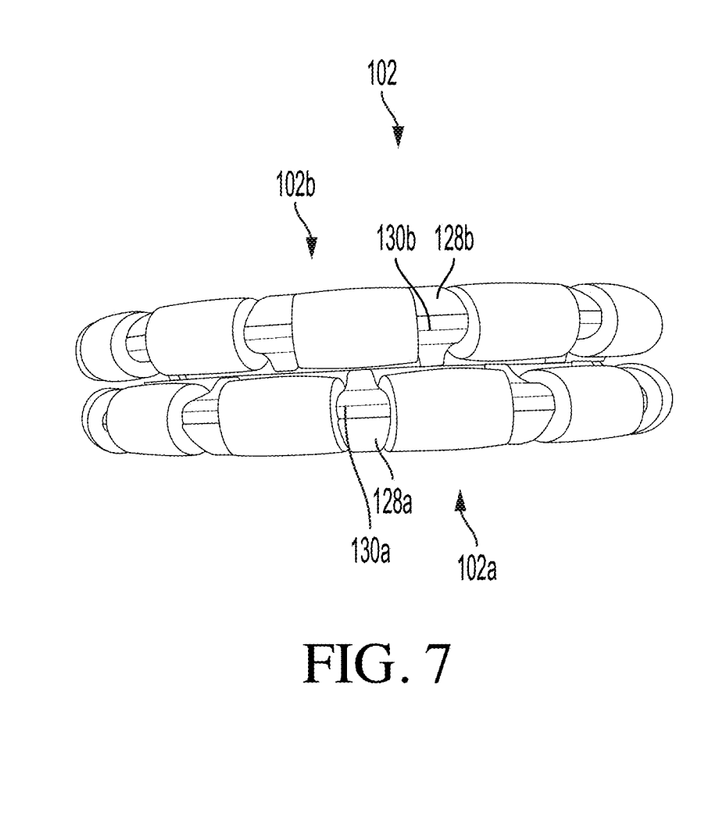
FIG. 7 illustrates a side view of a wheel in accordance with an exemplary embodiment of the present disclosure.

Referring now to FIG. 7, perspective view of one embodiment (e.g., a prototype) of first wheel 102, including subwheels 102a and 102b, is illustrated. In the illustrated embodiment, subwheel 102a includes a first portion 128a (e.g., a plate, an outer plate, etc.) and a second portion 130a (e.g., a plate, an inner plate, etc.). Similarly, subwheel 102b includes a first portion 128b (e.g., a plate, an outer plate, etc.) and a second portion 130b (e.g., a plate, an inner plate, etc.).

Figure 8:
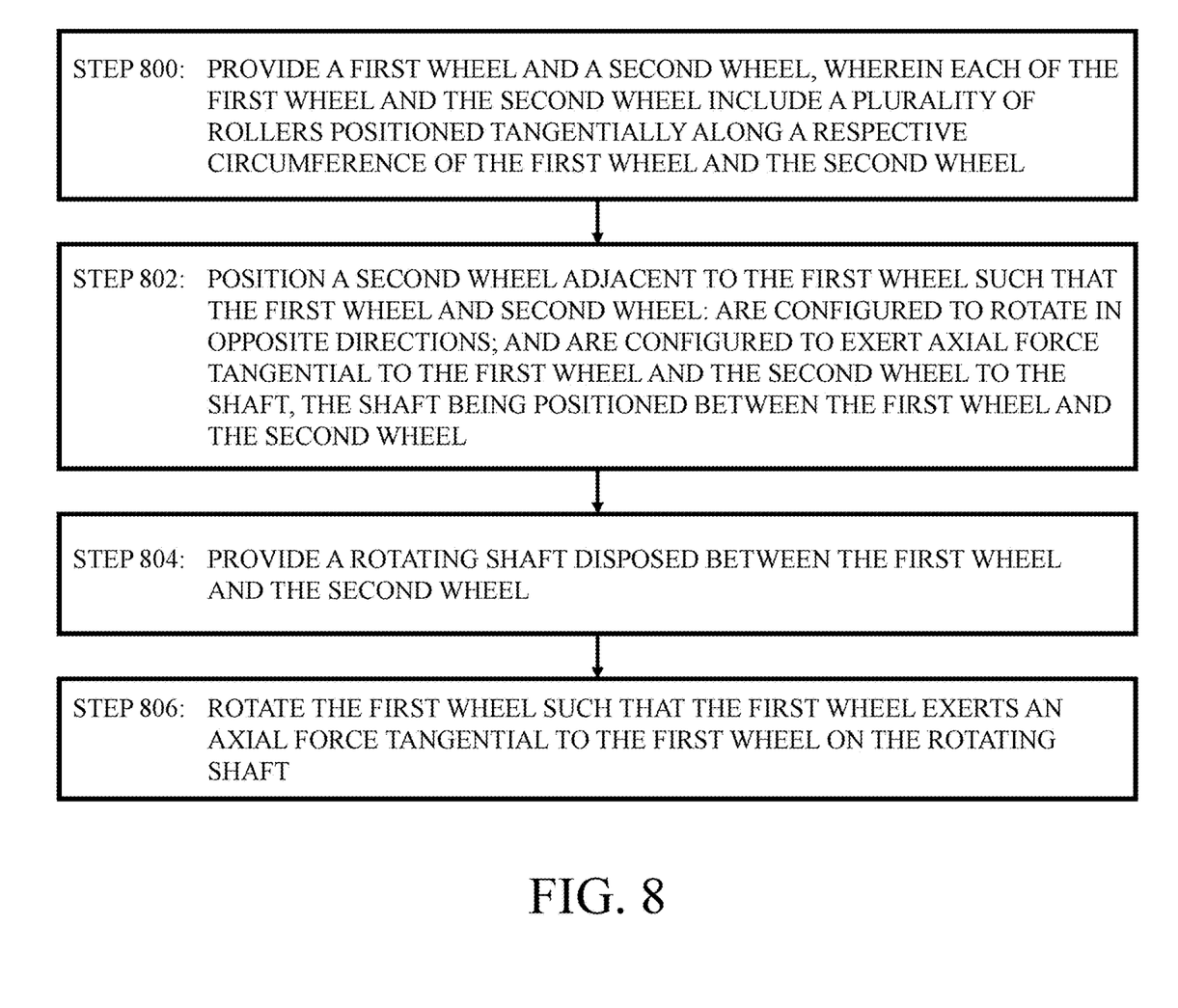
FIG. 8 is a flow diagram illustrating a method of axial positioning of a rotating shaft in accordance with an exemplary embodiment of the present disclosure.

FIG. 8 is a flow diagram illustrating an exemplary method of axial positioning of a rotating shaft. As is understood by those skilled in the art, certain steps included in the flow diagram may be omitted; certain additional steps may be added; and the order of the steps may be altered from the order illustrated—all within the scope of the invention.

In Step 800, a first wheel and a second wheel are provided, wherein each of the first wheel and the second wheel includes a plurality of rollers positioned tangentially along a respective circumference of the first wheel and the second wheel. In Step 802, a second wheel is positioned adjacent to the first wheel such that the first wheel and second wheel are configured to rotate in opposite directions and are configured to exert axial force tangential to the first wheel and the second wheel to the shaft, the shaft being positioned between the first wheel and the second wheel. In Step 804, a rotating shaft disposed between the first wheel and the second wheel is provided. In Step 806, the first wheel is rotated such that the first wheel exerts an axial force tangential to the first wheel on the rotating shaft.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A system for axial positioning of a rotating shaft, the system comprising:
a first wheel; and
a second wheel positioned adjacent to the first wheel such that the first wheel and second wheel:
are configured to rotate in opposite directions; and
are configured to exert axial force tangential to the first wheel and the second wheel to a shaft positioned between the first wheel and the second wheel;
wherein each of the first wheel and the second wheel each comprise a plurality of rollers positioned tangentially along a circumference of the first wheel and the second wheel, and
wherein the first wheel further comprises two axially offset rings of rollers.

2. The system of claim 1, wherein the second wheel comprises a single ring of rollers.

3. The system of claim 1, wherein the first wheel and the second wheel are each configured to be driven by a ferromagnetic coupling.

4. The system of claim 1, wherein at least one of the first wheel and the second wheel are configured to be driven by a ferromagnetic coupling.

5. The system of claim 1, wherein the first wheel comprises a plurality of magnets configured to be magnetically coupled to a second magnet and driven by a drive system.

6. The system of claim 1, further comprising:
a rod coupled to the second wheel, the rod being configured to translate second wheel to allow loading of a shaft; and
a spring, the spring being connected to the rod such that the spring can impose a spring force on the rod.

7. The system of claim 6, further comprising a lever pivotally coupled to the rod.

8. The system of claim 1, wherein the first wheel comprises a first subwheel and a second subwheel.

9. The system of claim 1, further comprising a housing portion at least partially enclosing the first wheel and the second wheel.

10. A system for axial positioning of a rotating shaft, the system comprising:
a shaft;
a first wheel; and
a second wheel positioned adjacent to the first wheel such that the first wheel and second wheel:
are configured to rotate in opposite directions; and
are configured to exert axial force tangential to the first wheel and the second wheel to the shaft, the shaft being positioned between the first wheel and the second wheel;
wherein each of the first wheel and the second wheel comprise a plurality of rollers positioned tangentially along a respective circumference of the first wheel and the second wheel, and
wherein the first wheel further comprises two axially offset rings of rollers.

11. The system of claim 10, wherein the shaft is selected from the group consisting of: a rotating shaft, a catheter, and a rotating catheter.

12. A method of axial positioning of a rotating shaft, the method comprising the steps of:

(a) providing a first wheel and a second wheel, wherein each of the first wheel and the second wheel comprise a plurality of rollers positioned tangentially along a respective circumference of the first wheel and the second wheel;
(b) positioning a second wheel adjacent to the first wheel such that the first wheel and second wheel:
   are configured to rotate in opposite directions; and
   are configured to exert axial force tangential to the first wheel and the second wheel to the shaft, the shaft being positioned between the first wheel and the second wheel;
(c) providing a rotating shaft disposed between the first wheel and the second wheel; and
(d) rotating the first wheel such that the first wheel exerts an axial force tangential to the first wheel on the rotating shaft, and
wherein the first wheel comprises two axially offset rings of rollers.

13. A system for translating motion across a sterility drape, the system comprising:
   a driving member, the driving member including:
      a first housing; and
      a first wheel within the first housing, the first wheel including a first magnet; and
   a driven member, the driven member including:
      a second housing;
      a second wheel within the second housing, the second wheel including a second magnet and two axially offset rings of rollers; and
      a third wheel within the second housing and positioned adjacent to the second wheel such that the second wheel and the third wheel:
         are configured to rotate in opposite directions; and
         are configured to exert axial force tangential to the second wheel and the third wheel to a shaft positioned between the second wheel and the third wheel,
      wherein each of the second wheel and the third wheel each comprise a plurality of rollers positioned tangentially along a circumference of the second wheel and the third wheel, and
   wherein the driven member can be removably mounted on the driving member over a sterility drape applied to the driving member such that rotational force can be transferred through magnetic coupling across the first housing, the sterility drape, and the second housing.

14. The system of claim 13, wherein the first magnet of the driving member is a first plurality of magnets and the second magnet of the driven member is a second plurality of magnets, the second plurality of magnets having a corresponding number of magnets to the first plurality of magnets.

* * * * *